United States Patent
Mermer et al.

(10) Patent No.: US 9,562,901 B2
(45) Date of Patent: Feb. 7, 2017

(54) A25 BACTERIOPHAGE LYSIN

(71) Applicant: Alere Scarborough, Inc., Scarborough, ME (US)

(72) Inventors: Brion Mermer, Gray, ME (US); William J. Palin, Cape Elizabeth, ME (US); Nancy Turcotte, Auburn, ME (US)

(73) Assignee: Alere Scarborough, Inc., Scarborough, ME (US)

( * ) Notice: Subject to any disclaimer, the term of this patent is extended or adjusted under 35 U.S.C. 154(b) by 0 days.

(21) Appl. No.: 14/561,776

(22) Filed: Dec. 5, 2014

(65) Prior Publication Data

US 2015/0198595 A1  Jul. 16, 2015

Related U.S. Application Data

(62) Division of application No. 13/575,217, filed as application No. PCT/US2011/022383 on Jan. 25, 2011, now Pat. No. 8,951,532.

(60) Provisional application No. 61/298,039, filed on Jan. 25, 2010.

(51) Int. Cl.
| | |
|---|---|
| *C12Q 1/00* | (2006.01) |
| *C12Q 1/68* | (2006.01) |
| *G01N 33/53* | (2006.01) |
| *G01N 33/554* | (2006.01) |
| *G01N 33/569* | (2006.01) |
| *C07K 14/005* | (2006.01) |
| *C12N 1/06* | (2006.01) |

(52) U.S. Cl.
CPC ....... *G01N 33/56944* (2013.01); *C07K 14/005* (2013.01); *C12N 1/06* (2013.01); *C12N 2795/00022* (2013.01); *G01N 2469/10* (2013.01); *G01N 2800/26* (2013.01)

(58) Field of Classification Search
CPC .......... C12Q 1/00; C12Q 1/14; C12Q 1/6888; C12Q 1/689; C12Q 1/70; C12Q 2527/125
See application file for complete search history.

(56) References Cited

U.S. PATENT DOCUMENTS

| | | | | |
|---|---|---|---|---|
| 5,604,109 A | * | 2/1997 | Fischetti | .................. C12Q 1/14 435/29 |
| 2006/0160121 A1 | | 7/2006 | Mounts et al. | |
| 2007/0025978 A1 | | 2/2007 | Yoong et al. | |

OTHER PUBLICATIONS

Hill et al., (J. of Bacteriol. 1981. vol. 145(2):696-703).*
Ma et al. (Vet. Microbiol. 2008. vol. 132. Issue 3-4, pp. 340-347).*
Celia, et al. "Characterization of bacteriophage lysin (Ply700) from *Streptococcus uberis*," Veterinary Microbiology; 130(Nos. 1-2): 107-117 (Jul. 27, 2008).
Hill, et al. "Identification of Lysin Associated with a Bacteriophage (A25) Virulent for Group A Streptococci," Journal of Bacteriology; 145(2): 696-703 (Feb. 1981).

(Continued)

*Primary Examiner* — Ja'Na Hines
(74) *Attorney, Agent, or Firm* — Foley Hoag LLP

(57) ABSTRACT

The invention relates to the identification, sequencing, and isolation of an A25 bacteriophage lysin gene that expresses a protein involved in the lysis of bacterial cells during the phage life cycle. The invention further relates to methods for lysing certain bacteria using lysin, which are useful for example in a diagnostic procedure designed to detect these bacteria.

10 Claims, 12 Drawing Sheets

(56) References Cited

OTHER PUBLICATIONS

Nelson, et al. "Prevention and elimination of upper respiratory colonization of mice by group A streptococci by using a bacteriophage lytic enzyme," PNAS; 98(7):4107-4112 (Mar. 27, 2001).
International Search Report PCT/US11/22383 dated May 27, 2011.
U.S. Appl. No. 13/575,217, filed Jan. 25, 2011.

\* cited by examiner

DNA and "deduced" protein sequence A25 lysin

DNA and "deduced" protein sequence A25 lysin

Figure 1 (cont.)
DNA and "deduced" protein sequence A25 lysin

Figure 1 (cont.)
DNA and "deduced" protein sequence A25 lysin

DNA and "deduced" protein sequence A25 lysin

Figure 1 (cont.)
DNA and "deduced" protein sequence A25 lysin

Figure 2

- Sequence comparison with most related previously disclosed lysin

```
Identity = (387/481) 80.5% YP_950557.1 putative lysin [Streptococcus phage SMP
Query: 1     MAIETEKAISWMVARQGAVSYSMDYRNGPSSYDCSSAIYYALMSAGAISAGWAVNTEYMH 60
             M I  E AI WM  R G V YSMDYRNGP+S+DCSS++YYALM+ GAISAGWAVNTEY H
Sbjct: 1     MTINIETAIRWMTDRVGLVKYSMDYRNGPNSFDCSSSVYYALMAGGAISAGWAVNTEYEH 60

Query: 61    DWLIKNGYVLIAENQDWNSQRGDVVIWGLRGQSAGAGGHVVMFVDSDNIIHCNYANNGIT 120
             DWLIKNGY LIAENQDW+++RGD+ IWG RGQS+GAGGH  +FVD DNIIHCNYANN IT
Sbjct: 61    DWLIKNGYKLIAENQDWDAKRGDIFIWGRRGQSSGAGGHTGIFVDPDNIIHCNYANNSIT 120

Query: 121   INNYNQTAASAGWMYSYVYRLATPATTSTAGKSLDTLVKETLAGNYGNGEMRKAALGNQY 180
             INNYNQTAA++GWMY YVYRL   TTS AGK+LDTLVKETLAG YGNG+ RKAALGNQY
Sbjct: 121   INNYNQTAAASGWMYCYVYRLGNQPTTSPAGKTLDTLVKETLAGKYGNGDQRKAALGNQY 180

Query: 181   DAVMVVINGKSTTAQKSVDQLAQEVIAGKHGNGEGRKKALGSQYDAVQKRVTEMLKTSTS 240
             +AVM VINGK+T  +K+VDQLAQEVI GKHGNGE RKK+LG  YDAVQKRVTE+L+ STS
Sbjct: 181   EAVMAVINGKATAPKKTVDQLAQEVIQGKHGNGEDRKKSLGPDYDAVQKRVTEILQGSTS 240

Query: 241   GNTSKTPSEPSNSVVVNSSTEPKTEETGATGKATDTKITKEDGDLSFNGAILKKSVLDVI 300
             GN  K  S+   + VVNSSTEPKTEET ATGKATDTKITKEDGDLSFNGAILKKSVLDVI
Sbjct: 241   GNAPKLASDAPKNEVVNSSTEPKTEETWATGKATDTKITKEDGDLSFNGAILKKSVLDVI 300

Query: 301   LAKCKEHNILPSYAITVLHFEGLWGTSAVGKADNNWGGMTWTGKGERPSGVTVTQGTARP 360
             LA CK+H+ILPSYA+T LH+EGLWGTSAVGKADNNWGGMTWTGKGERPSGVTVTQGTARP
Sbjct: 301   LANCKKHDILPSYALTILHYEGLWGTSAVGKADNNWGGMTWTGKGERPSGVTVTQGTARP 360

Query: 361   ANEGGHYMHYASVDDFLTDWFYLLRSGGSYKVSGAKTFSDAVKGMFKVGGSVYDYAASGF 420
             A EGGHYMHYASVDDFLTDWFYLLRSGGSYKVSGAKTFSDAVKGMFK+GG+VYDYAASGF
Sbjct: 361   ACEGGHYMHYASVDDFLTDWFYLLRSGGSYKVSGAKTFSDAVKGMFKIGGAVYDYAASGF 420

Query: 421   DSYIVGASSRLKAIEQENGSLDKFDKATDIGVGSKDQIDITIAGIEVTINGITYELTKKP 480
             DSYI+GASSRLKAIE ENGSLDKFDK T    VG D+I++TI GIE++ING+TY L+KKP
Sbjct: 421   DSYIIGASSRLKAIEAENGSLDKFDKQTVTDVGQSDKIEVTIEGIEISINGVTYTLSKKP 480
```

(A)

SDS-Polyacrylamide gel analysis of purified recombinant His-tagged PlyA. After expression in E. coli Origami DE3 (emd bioscience), His-tagged PlyA was purified on a Ni-NTA affinity column (Qiagen) as described above, and analyzed on a 4-20% SDS polyacrylamide gel after reduction and denaturation. The mobility was as predicted (52.5kD) based on the DNA sequence.

Figure 3
(B)

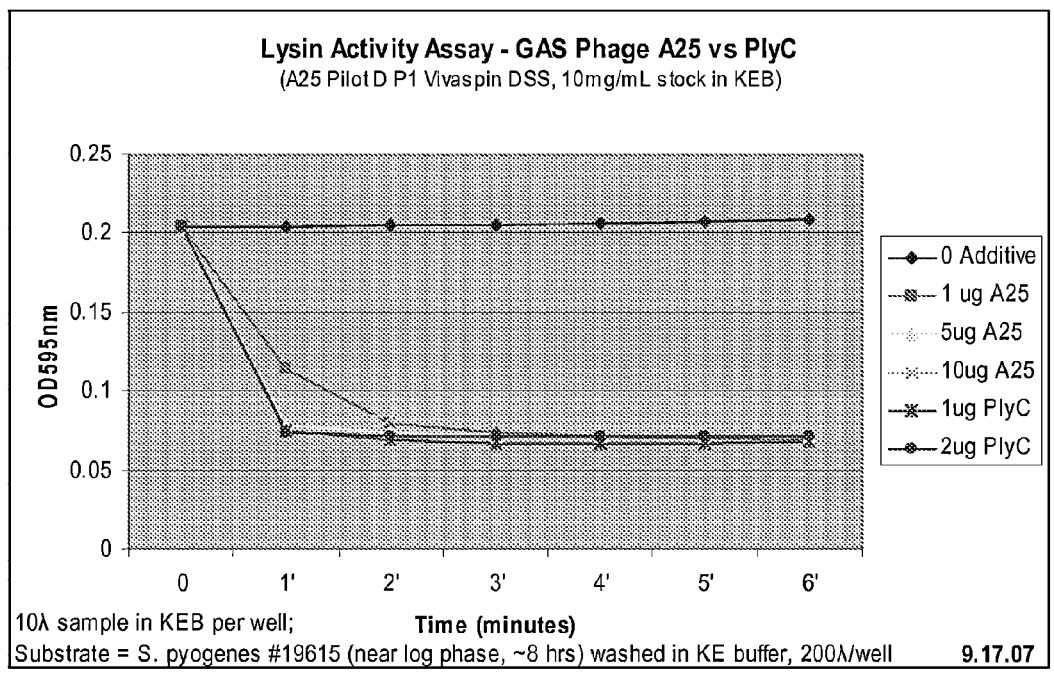

Comparison of PlyA Activity to PlyC. S. pyogenes #19615, near log phase growth after 8 hours of incubation, was washed in KE buffer (0.1M KPO$_4$, 5mM EDTA, pH 6.7) and plated in microtiter wells. Dilutions of NiNTA-purified PlyA and PlyC were prepared in KEB buffer (0.1M KPO$_4$, 5mM EDTA, 3mM BME, pH 6.7) and added to S. pyogenes substrate in wells at the indicated quantities. Lysin activity was assayed by determining the reduction in turbidity over a 6-minute interval.

Figure 4

Phage A25 gene DNA sequence

```
5' atgGCAATAGAGACTGAAAAAGCCATTTCTTGGATGGTAGCTAGACAAGGGGCTGTTTCTTATTCCATGGATTACCGAAATGGTCCAAGC   90
5' TCCTATGACTGCTCAAGTGCTATTTATTATGCTTTGATGTCAGCAGGTGCTATCTCGCTGGCTGGGCTGTAAATACAGAATATATGCAT  180
5' GATTGGCTTATCAAAAATGGATATGTATTCATTGCAGAAAAATCAAGATTGGAATACCAAAGGGGTGATGTTGTTATTTGGGGCTACGT  270
5' GGTCAGTCTGCTGGAGCTGGTGGTCATGTCGTAATGTTTGTAGATTCAGACAACATCATTCACTGTAATTATGCCAATAATGGCATTACC  360
5' ATCAATAACTACAATCAGACCGCTGCTAGCGCTGCCTGGCTGGATGTATTCTTATGTTACCGTTTAGCCACCCAGCAACAACTTCAACGGCT  450
5' GGGAAAAGTCTCGATACCTTAGTTAAGGAAACCTGGCTGGTAACTACGGTAACGAGAAATGCGTAAGGCAGCCCTTGGTAATCAATAT  540
5' GATGCTGTCATGGTAGTCATCAATGGCAAATCTACGACAGCTCAAAAGTCAGTTGACCAACTGCGGCCAGGAAGTGATTGCTGGTAAGCAC  630
5' GGTAACGGTGAAGGCCGTAAAACACCTGGGACCACTTGGGAGCCAGTATGCGAAATGCTAAAAACTAGTACATCA  720
5' GGAAACACCTCTAAAACACCATCAGAGCCATCTAATAGCGTGGTGGTGTTGTCCTTAACGGTGCAATCCTGAAAAAATCTGTCCTTGATGTTATC  810
5' GGTAAAGCGACAGATACCAACAATCACTGAAGAAGATGTGACTTGTCCTTAACCGTTCTACACTTTGAGGGCTTTGACTGTCACCCAAGGAACACCAAGACCA  900
5' CTTGCTAAGTGTAAGGAACAACTGGGAGCCATGACTATATGCACTATGCCTGGTAACTGGTCTAGATGACTTTCTACAGATTGGTTCTACCTGCTACGTTCAGGAGGTAGCTAC  990
5' AAGGCAGATAACAACTGGGAGCCATGACTATATGCACTATGCCTGGTAACTGGTCTAGATGACTTTCTACAGATTGGTTCTACCTGCTACGTTCAGGAGGTAGCTAC 1080
5' GCTAATGAGGGTGACATTATATGCACTATGCCTTAGCGATGCTGTCAAAGGCATGCTATTGAGCAGGAAAACGGTCTTCTTTGACAAGTTTGATAAAGCTACCGACATT 1170
5' AAGGTTTCAGGAGCCAAAACCTTAGCGATGCTGTCAAAGGCATGCTATTGAGCAGGAAAACGGTCTTCTTTGACAAGTTTGATAAAGCTACCGACATT 1260
5' GATAGCTACATCGTTGGAGCTTCAGCCGTCTCAAGGCATGCTATTGAGCAGGAAAACGGTCTTCTTTGACAAGTTTGATAAAGCTACCGACATT 1350
5' GGTGTCGGTAGCAAAGACCCAGATTGACATTACCATTGCAGGTATTGAAGTTACCATTGCAGGTATTGAACTGACTAAAAGCCA 1440
5' GTTtga
```

Figure 5

Phage A25 protein sequence

```
MAIETEKAISWMVARQGAVSYSMDYRNGPSSYDCSSAIYALMSAGAISAGWAVNTEYMHDWLIKNGYVLIAENQDWNSQRGDVIWGLR    90
GQSAGAGGHVVMFVDSDNIIHCNYANNGITINNYNQTAASAGWMYSYVYRLATPATTSTAGKSLDTLVKETLAGNYGNGEMRKAALGNQY   180
DAVMVVINGKSTTAQKSVDQLAQEVIAGKHGNGEGRKKALGSQYDAVQKRVTEMLKTSTSGNTSKTPSEPSNSVVVNSSTEPKTEETGAT   270
GKATDKITKEDGDLSFNGAILKKSVLDVILAKCKEHNILPSYAITVLHFEGLWGTSAVGKADNNWGGMTWTGKGERPSGVTVTQGTARP    360
ANEGGHYMHYASVDDFLTDWFYLLRSGGSYKVSGAKTFSDAVKGMFKVGGSVYDYAASGFDSYIVGASSRLKAIEQENGSLDKFDKATDI   450
GVGSKDQIDITIAGIEVTINGITYELTKKP
```

A25 BACTERIOPHAGE LYSIN

RELATED APPLICATIONS

This application is a divisional application of U.S. Application No. 13/575,217 filed Oct. 9, 2012; which is a 371 national stage application of PCT/US11/022383, filed Jan. 25, 2011, which claims the benefit of priority to U.S. Provisional Patent Application Ser. No. 61/298,039, filed Jan. 25, 2010; the contents of which are hereby incorporated by reference.

FIELD OF THE INVENTION

The invention relates to novel proteins and nucleic acids isolated from A25 bacteriophage and diagnostic and therapeutic uses of these nucleic acids and polypeptides and related pharmaceutical compositions useful in treating Streptococcal infections. The invention further relates to the identification, isolation and cloning of specific genes from the A25 bacteriophage, specifically the A25 bacteriophage lysin, termed PlyA, and the use of this gene and gene products to aid in diagnosis of infections caused by Group A Streptococci and for prophylactic and therapeutic use to treat or prevent Group A Streptococcal infections.

BACKGROUND OF THE INVENTION

Streptococcus pyogenes is a group A streptococcal gram-positive bacterium that is the etiological agent of several diseases in humans, including pharyngitis and/or tonsillitis, skin infections (impetigo, erysipelas, and other forms of pyoderma), acute rheumatic fever (ARF), scarlet fever (SF), poststreptococcal glomerulonephritis (PSGN), and a toxic shock-like syndrome (TSLS). On a global basis, ARF is the most common cause of pediatric heart disease. For example, it is estimated that in India, more than six million school-aged children suffer from rheumatic heart disease. In the United States, "sore throat" is the third most common reason for physician office visits and *S. pyogenes* is recovered from about 30% of children with this complaint. There are about 25-35 million cases of streptococcal pharyngitis per year in the United States, responsible for about 1-2 billion dollars per year in health care costs.

SUMMARY OF THE INVENTION

The present invention relates to the isolation and elucidation of the nucleic acid and protein sequence of A25 bacteriophage, which is specific for Group A streptococci, and the diagnostic and therapeutic uses of these nucleic acid and polypeptide sequences. Furthermore, an open reading frame has been identified, and the deduced polypeptide is described. The available sequence data now provides the means by which diagnostic and therapeutic utility can be carried out using the lytic properties associated with isolated PlyA lysin.

Accordingly, a first aspect of the invention provides for the isolation and elucidation of the full length nucleic acid sequence of A25 bacteriophage lysin, provided herein as SEQ ID NO: 1. A second aspect of the invention provides for the isolation and elucidation of the full length polypeptide sequence of A25 bacteriophage lysin, provided herein as SEQ ID NO: 2. A description of the sequences and potential diagnostic and therapeutic utility of these sequences is provided below.

Accordingly another aspect of the invention provides for methods of diagnosing the presence of a pathogenic streptococcal infection. In a specific embodiment, a clinical sample suspected of harboring Group A streptococcus cells is pretreated with a PlyA polypeptide provided herein. Pretreatment of the clinical sample lyses Group A streptococcus cells, if present in the sample, rendering cell lysate components accessible to antibodies used in detection.

A method of diagnosing a pathogenic streptococcal infection, may comprise: a) providing a patient sample suspected of harboring a streptococcus; b) contacting the sample with a PlyA polypeptide; and c) detecting a Group A streptococcal analyte present in the sample, wherein the presence of the Group A streptococcal analyte in the sample, indicates the presence of a streptococcal infection in the subject. In one aspect, the PlyA polypeptide comprises an amino acid sequence with greater than 80% sequence identity to SEQ ID NO: 2. In another aspect, the PlyA polypeptide comprises SEQ ID NO: 2.

Diagnostic testing formats, including ELISA assays, lateral flow assays, or radioimmunoassays may be contemplated for use with the present invention. In these formats, one can utilize a PlyA protein directly and/or one may prepare antibodies to a streptococcal antigen as noted herein for use in kits to monitor the presence of pathogenic streptococci in a patient sample. The procedures for ELISA or radioimmunoassays are known to those skilled in the art.

PlyA may be used to directly detect Group A streptococcus cells in a clinical sample. For example, a binding domain of PlyA may be labeled with, e.g., a fluorescent chemical or protein using methods known to those skilled in the art, and the labeled PlyA is then incubated directly with a sample taken from a subject suspected of harboring a pathogenic streptococci. The observation of bound label, e.g., fluorescence, in the sample is indicative of the presence of a pathogenic streptococcal infection.

A yet further embodiment provides for the use of PlyA in an activity-based assay, such as a luciferin-luciferase assay, to aid in diagnosing pathogenic streptococcal infections. In such an assay format, a sample suspected of harboring a pathogenic streptococcus is incubated directly with PlyA. If the sample contains a pathogenic streptococcus, the PlyA will bind to the bacteria, resulting in lysis of the bacteria and subsequent release of ATP or other components normally present in the cytoplasm of the bacterial cell, such as enzymes. The lysate is then tested in a luciferin-luciferase assay. In another embodiment, the sample suspected of harboring a pathogenic streptococcus may be added directly to PlyA concurrently with luciferin-luciferase without the need to collect the cell lysate first before adding it to the luciferin-luciferase. If a pathogenic streptococcus is present in the sample, the release of ATP from the lysed bacteria will trigger a positive reaction in the luciferin-luciferase system, resulting in release of measurable light from the reaction mixture.

It is envisioned that PlyA may be used for treating or preventing bacterial infections, comprising administering a therapeutically effective amount of PlyA. In a yet further embodiment of the invention, the PlyA is prepared as a pharmaceutical composition with a pharmaceutically acceptable carrier for use in treating bacterial infections, including infections caused by pathogenic streptococci of Group A. It is envisioned that the composition comprising PlyA may be useful in treating streptococcal infections in mammals, including, but not limited to, humans. A yet further embodiment provides for the use of the pharmaceutical compositions for treatment of streptococcal pharyngitis and other Group A streptococcal diseases. A yet further embodiment provides for the use of the polypeptides of the present invention, that is, the A25 bacteriophage PlyA lytic enzyme, including biologically active PlyA fragments, mutants, variants, analogs or derivatives thereof for the preparation of a medicament for the treatment of a bacterial infection. In another preferred embodiment, the invention provides for the use of the polypeptides of the present invention, that is, the A25 bacteriophage PlyA lytic enzyme, including fragments, mutants, variants, analogs or derivatives thereof for the preparation of a medicament for the treatment of streptococcal infections.

Another aspect of the invention provides for the generation of antibodies specific for PlyA. In a preferred embodiment, the antibodies are monoclonal antibodies specific for PlyA, or subunits or fragments thereof. In a yet further embodiment, the antibodies are polyclonal antibodies prepared in mice, rats, guinea pigs, rabbits, goats, sheep, horses, pigs, cows, or any other mammal generally used in the art for generation of polyclonal antibodies. In another embodiment, the antibodies may be chimeric antibodies, humanized antibodies, single chain antibodies or fragments thereof. A further embodiment provides for an immortal cell line that produces a monoclonal antibody that is specific for PlyA or subunits or fragments thereof.

One further embodiment of the invention may use an antibody to PlyA or fragments thereof, or antibodies may be prepared to PlyA or fragments thereof, and the antibody may be labeled (cg. with fluorescein or other known fluorescent proteins or chemicals), coupled to the bacteriophage protein and used to monitor binding of the specific protein to the bacteria in a patient sample, thus aiding in detection of pathogenic streptococci. Alternatively, a PlyA protein may be fluorescein labeled directly and used to detect the presence of pathogenic streptococci in a patient sample.

Another aspect of the invention provides for methods of preventing or treating bacterial infections comprising administering a therapeutically effective dose of a composition comprising a therapeutically effective amount of PlyA having a sequence as set forth in SEQ ID NO: 2.

Another aspect of the invention provides for pharmaceutical compositions comprising a therapeutically effective amount of PlyA as set forth is SEQ ID NO: 2 and a pharmaceutically acceptable carrier. A specific embodiment may include a pharmaceutical composition designed for use in treatment of infections caused by streptococcus group A. Another embodiment may include a pharmaceutical composition designed for use in treatment of topical or systemic infections, or infections that are non-responsive to other antibiotic modalities. A yet further embodiment provides for veterinary use of the pharmaceutical compositions of the present invention. A preferred embodiment is for use in treating infections in mammals, including but not limited to, human subjects. Another embodiment provides for a composition comprising the polypeptides of the present invention, that is, the A25 bacteriophage PlyA lytic enzyme, including fragments, mutants, variants, analogs or derivatives thereof for use in decontaminating inanimate surfaces to eliminate possible contamination with Group A streptococci.

Other advantages of the present invention will become apparent from the ensuing detailed description taken in conjunction with the following illustrative drawings.

BRIEF DESCRIPTION OF THE DRAWINGS

FIG. 2 shows a sequence alignment of PlyA (SEQ ID NO: 2) with a putative lysin for Streptococcus phage. The sequence identity between the two sequences is 80.5%, the highest sequence similarity found between SEQ ID NO: 2 and a previously disclosed lysin.

FIG. 4 shows the DNA sequence of the Phage A25 gene.

FIG. 5 shows the Phage A25 protein sequence.

DETAILED DESCRIPTION

Figure 1:
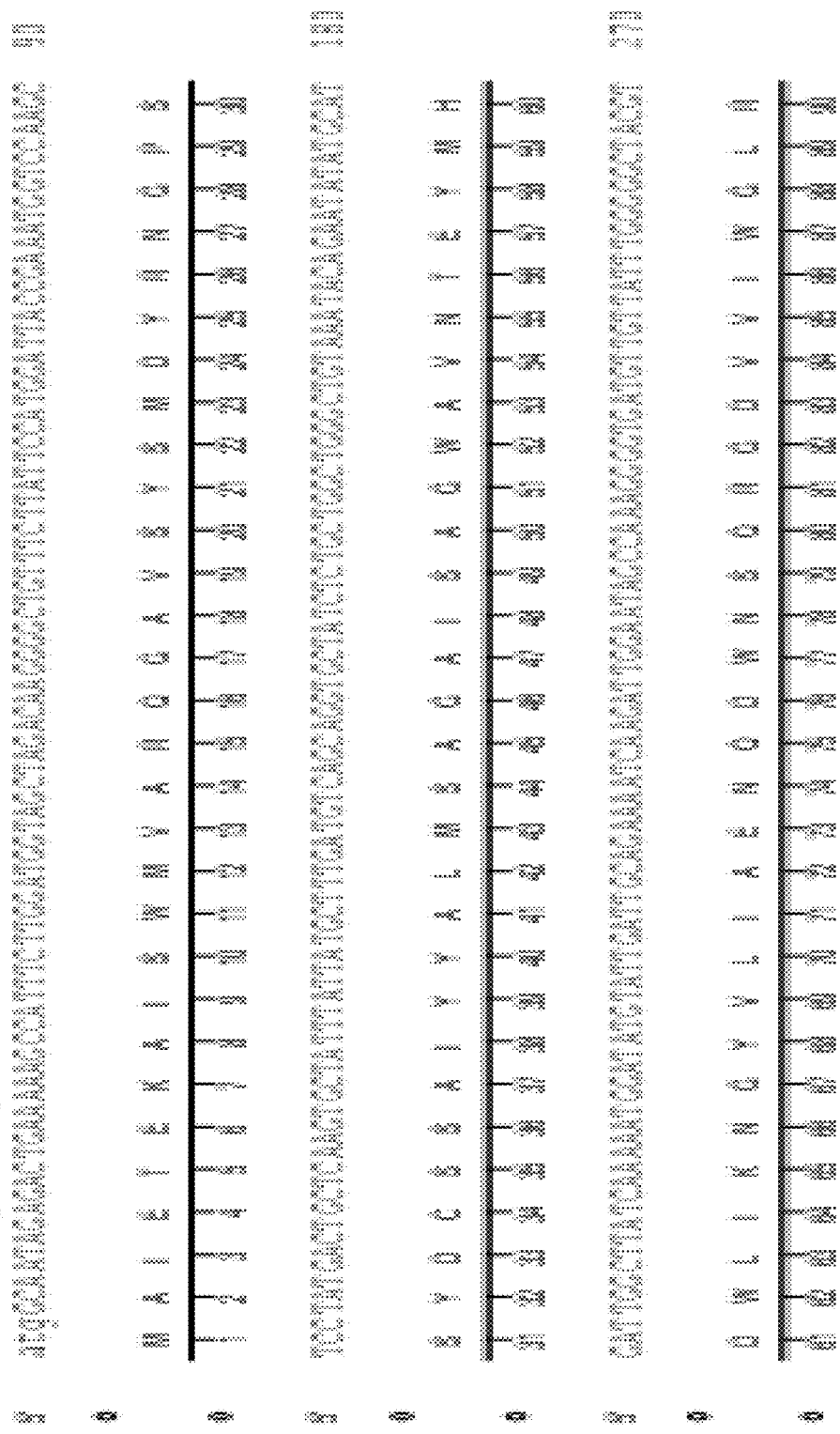
FIG. 1 shows a DNA and "deduced" protein sequence for A25 lysin (PlyA).
Figure 1:
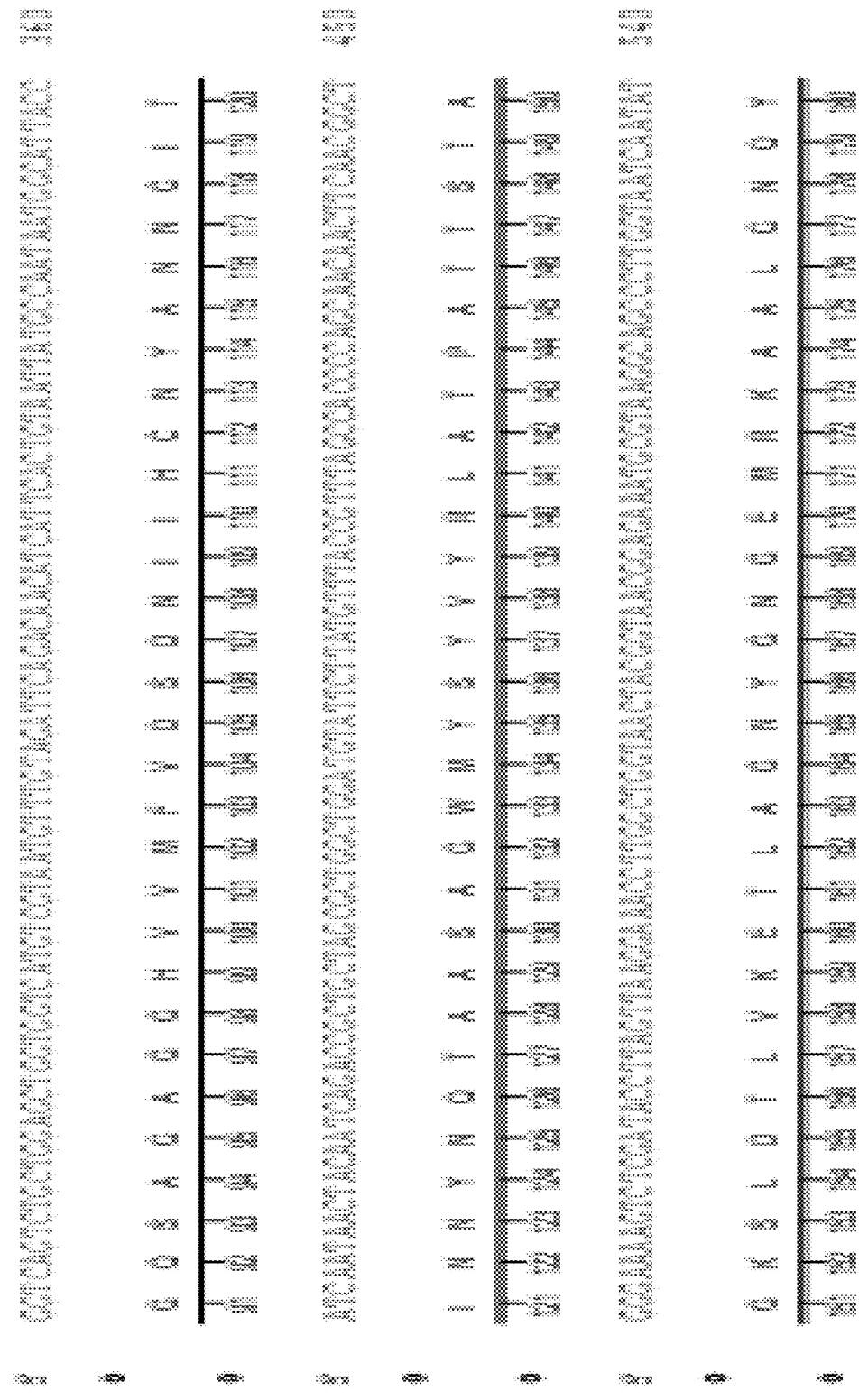
Figure 1:
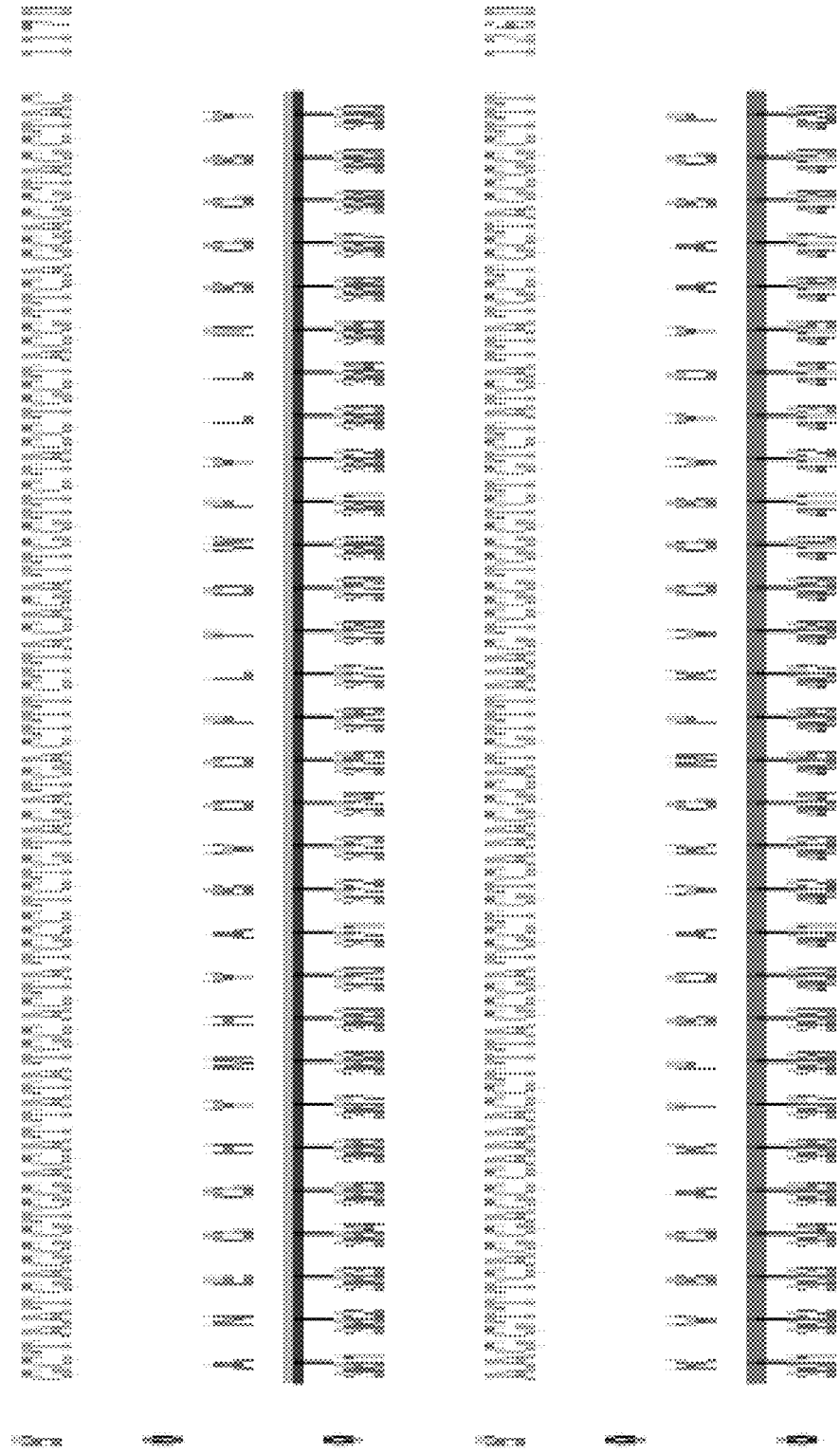
Figure 3:
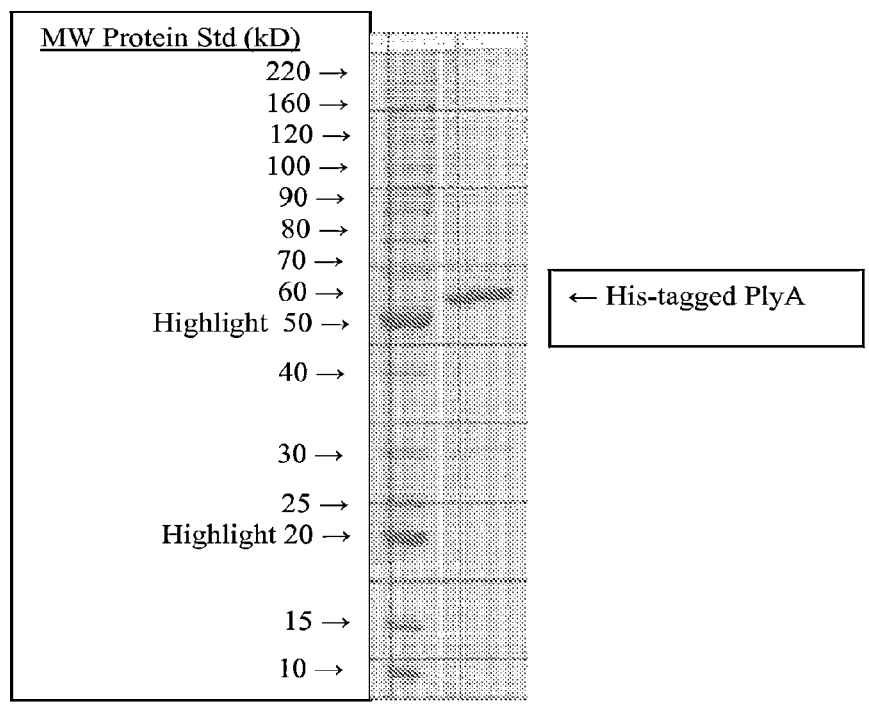
FIG. 3(a) shows a SDS-Polyacrylamide gel analysis of purified recombinant His-tagged PlyA.
FIG. 3(b) shows a lysin activity assay for GAS Phage A25 vs. PlyC.

The invention relates to the identification, sequencing, and isolation of an A25 bacteriophage lysin gene that expresses a protein involved in the lysis of bacterial cells during the phage life cycle. The invention further relates to methods for lysing certain bacteria using lysin, which are useful for example in a diagnostic procedure designed to detect these bacteria. The embodiments described herein provide for increased assay sensitivity/specificity over previously described assays.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

Definitions

"Treatment" refers to the administration of medicine or the performance of medical procedures with respect to a patient, for either prophylaxis (prevention) or to cure the infirmity or malady in the instance where the patient is afflicted.

The term "antibody" as used herein includes intact molecules as well as fragments thereof, such as Fab and F(ab')$_2$, which are capable of binding the epitopic determinant. The antibodies may be monoclonal, polyclonal, chimeric, humanized, or single chain antibodies, or fragments thereof. Antibodies that binds a polypeptide PlyA, or subunits or fragments thereof, can be prepared using intact dimers, polypeptides or fragments-containing small peptides of interest as the immunizing antigen attached to a carrier molecule. Commonly used carriers that are chemically coupled to peptides include bovine serum albumin and thyroglobulin. The coupled peptide is then used to immunize the animal (e.g., a mouse, rat or rabbit).

A "therapeutically effective amount" or "therapeutically effective dose" is an amount or dose sufficient to decrease, prevent or ameliorate the symptoms associated with the bacterial infection.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Analog" as used herein, refers to a nucleotide, a protein, or a polypeptide that possesses similar or identical activity or function(s) as the nucleotide, protein or polypeptide having the desired activity and therapeutic effect of the present invention (e.g., Group A streptococcal cell-wall lytic activity; or having the ability to aid in the diagnosis of streptococcal infections or prevent or treat streptococcal infections), but need not necessarily comprise a sequence that is similar or identical to the sequence of the preferred embodiment, such as that of SEQ ID NOS: 1 or 2, or possess a structure that is similar or identical to that of SEQ ID NOS: 1 or 2. As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues); or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of the preferred embodiment. The structure of a polypeptide can determined by methods known to those skilled in the art, including but not limited to, X-ray crystallography, nuclear magnetic resonance, and crystallographic electron microscopy.

"Derivative" refers to either a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide protein or polypeptide possesses a similar or identical function as the parent polypeptide.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

A "variant" (v) of polynucleotides or polypeptides, as the term is used herein, are polynucleotides or polypeptides that are different from a reference polynucleotide or polypeptide, respectively. Variant polynucleotides are generally limited so that the nucleotide sequence of the reference and the variant are closely related overall and, in many regions, identical. Changes in the nucleotide sequence of the variant may be silent. That is, they may not alter the amino acid sequence encoded by the polynucleotide. Where alterations are limited to silent changes of this type a variant will encode a polypeptide with the same amino acid sequence as the reference. Alternatively, changes in the nucleotide sequence of the variant may alter the amino acid sequence of a polypeptide encoded by the reference polynucleotide. Such nucleotide changes may result in amino acid substitutions, additions, deletions, fusions, and truncations in the polypeptide encoded by the reference sequence. Variant polypeptides are generally limited so that the sequences of the reference and the variant are that are closely similar overall and, in many regions, identical. For example, a variant and reference polypeptide may differ in amino acid sequence by one or more substitutions, additions, deletions, fusions, and truncations, which may be present or absent in any combination. Such variants can differ in their amino acid composition (e.g. as a result of allelic or natural variation in the amino acid sequence, e.g. as a result of alternative mRNA or pre-mRNA processing, e.g. alternative splicing or limited proteolysis) and in addition, or in the alternative, may arise from differential post-translational modification (e.g., glycosylation, acylation, phosphorylation, isoprenylation, lipidation).

A nucleic acid which is "hybridizable" to a nucleic acid of the present invention or to its reverse complement, or to a nucleic acid encoding a derivative, or to its reverse complement under conditions of low stringency can be used in the methods of the invention to detect the presence of a PlyA gene and/or presence or expression level of PlyA. By way of example and not limitation, procedures using such conditions of low stringency are as follows (see also Shilo and Weinberg, 1981, Proc. Natl. Acad. Sci. U.S.A. 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1%

SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency that may be used are well known in the art (e.g., as employed for cross-species hybridizations).

A nucleic acid which is "hybridizable" to a PlyA nucleic acid (e.g., having a sequence as set forth in SEQ ID NO: 1 or to its reverse complement, or to a nucleic acid encoding a derivative thereof, or to its reverse complement under conditions of high stringency) is also provided for use in the methods of the invention. By way of example and not limitation, procedures using such conditions of high-stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filter is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency that may be used are well known in the art.

A nucleic acid which is "hybridizable" to a PlyA nucleic acid (e.g., having a sequence as set forth in SEQ ID NO: 1 or to its reverse complement, or to a nucleic acid encoding a derivative thereof, or to its reverse complement under conditions of moderate stringency) is also provided for use in the methods of the invention. For example, but not limited to, procedures using such conditions of moderate stringency are as follows: filters comprising immobilized DNA are pretreated for 6 hours at 55 ° C. in a solution containing 6×SSC, 5× Denhardt's solution, 0.5%. SDS and 100 µg/ml denatured salmon sperm DNA. Hybridizations are carried out in the same solution with 5-20×10$^6$ cpm $^{32}$P-labeled probe. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Washing of filters is done at 37° C. for 1 hour in a solution containing 2×SSC, 0.1% SDS. Other conditions of moderate stringency that may be used are well known in the art. (see, e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols. 1994-1997 John Wiley and Sons, Inc.).

The terms "protein" and "polypeptide" are used interchangably herein.

General Description

The present invention provides methods for the elucidation of the nucleic acid and protein sequence of A25 bacteriophage lysin (PlyA), which is specific for Group A streptococci, and the diagnostic and therapeutic uses of these nucleic acid and polypeptide sequences. The invention provides for the full-length nucleic acid sequence of PlyA, as set forth in SEQ ID NO: 1. A sequence analysis of SEQ ID NO: 2 shows 80% sequence identity to a putative lysin for Streptococcus phage (FIG. 2), the highest sequence similarity found between SEQ ID NO: 2 and a previously disclosed lysin. Further analysis of the bacteriophage A25 DNA revealed four domains, which are identifiable based upon sequence comparison with other enzymes, including two "Cpl-7" domains are thought to mediate substrate binding.

Previous studies demonstrated that the lytic properties associated with an isolated lysin had therapeutic potential to eliminate streptococcal colonization (Nelson et al. (2001) Proc. Nat. Acad. Sci. USA. 98:4107-4112). Use of the sequence data provided herein provides means by which such diagnostic and therapeutic utility can be carried out. It is envisioned that PlyA may be used for treating or preventing bacterial infections, comprising administration of a therapeutically effective amount of a PlyA polypeptide provided herein.

Accordingly another aspect of the invention provides for methods of diagnosing the presence of a pathogenic streptococcal infection. In a specific embodiment, a clinical sample suspected of harboring Group A streptococcus cells is pretreated with a PlyA polypeptide provided herein. Pretreatment of the clinical sample lyscs Group A streptococcus cells, if present in the sample, rendering cell lysate components accessible to antibodies used in detection.

A method of diagnosing a pathogenic streptococcal infection, may comprise: a) providing a patient sample suspected of harboring a streptococcus; b) contacting the sample with a PlyA polypeptide; and c) detecting a Group A streptococcal analyte present in the sample, wherein the presence of the Group A streptococcal analyte in the sample, indicates the presence of a streptococcal infection in the subject. In one aspect, the PlyA polypeptide comprises an amino acid sequence with greater than 80%, 85%, 90%, 95%, 98%, or 99% sequence identity to SEQ ID NO: 2. In another aspect, the PlyA polypeptide comprises SEQ ID NO: 2.

Diagnostic testing formats, including ELISA assays, lateral flow assays, or radioimmunoassays may be contemplated for use with the present invention. In these formats, one can utilize a PlyA protein directly or one may prepare antibodies to such protein as noted herein for use in kits to monitor the presence of pathogenic streptococci in a patient sample. The procedures for ELISA or radioimmunoassays are known to those skilled in the art.

One aspect of the invention provides for methods of diagnosing the presence of a pathogenic streptococcal infection. In a preferred embodiment, PlyA or a fragment comprising a binding domain thereof, is labeled, e.g., with a fluorescent chemical or protein and the labeled PlyA is then incubated directly with a sample taken from a subject suspected of harboring a pathogenic streptococci. The observation of fluorescence in the sample is indicative of the presence of a pathogenic streptococcal infection. A yet further embodiment provides for the use of the PlyA, or a fragment comprising a binding domain thereof, in a luciferin-luciferase assay to aid in diagnosing pathogenic streptococcal infections. In this assay format, a sample suspected of harboring a pathogenic streptococcus is incubated directly with PlyA or a fragment comprising a binding domain thereof. If the sample contains a pathogenic streptococcus, the PlyA or fragment comprising a binding domain thereof will bind to the bacteria, resulting in lysis of the bacteria and subsequent release of ATP or other components normally present in the cytoplasm of the bacterial cell, such as enzymes. The lysate is then tested in a luciferin-lucifersase assay. In another embodiment, the sample suspected of harboring a pathogenic streptococcus may be added directly to the PlyA or fragment comprising a binding domain thereof concurrently with luciferin-luciferase without the need to collect the cell lysate first before adding it to the luciferin-luciferase. If a pathogenic streptococcus is present in the sample, the release of ATP from the lysed bacteria will trigger a positive reaction in the luciferin-luciferase system, resulting in release of measurable light from the reaction mixture.

In a yet further embodiment of the invention, PlyA is prepared as a pharmaceutical composition with a pharmaceutically acceptable carrier for use in treating bacterial infections, including infections caused by pathogenic streptococci of Group A. It is envisioned that the composition comprising PlyA may be useful in treating streptococcal infections in mammals, including, but not limited to, humans. A further embodiment provides for use of the pharmaceutical compositions for treatment specifically of Group A streptococcal infections, including streptococcal pharyngitis ("strep throat"), acute rheumatic fever, rheumatic fever, scarlet fever, acute glomerulonephritis, and necrotizing fasciitis. A yet further embodiment includes the use of the pharmaceutical compositions comprising PlyA for treatment of humans.

A further aspect of the invention provides for the generation of antibodies specific for PlyA. In a preferred embodiment, the antibodies are monoclonal antibodies specific for PlyA, or subunits or fragments thereof. In a yet further embodiment, the antibodies are polyclonal antibodies prepared in mice, rats, guinea pigs, rabbits, goats, sheep, horses, pigs, cows, or any other mammal generally used in the art for generation of polyclonal antibodies. In another embodiment, the antibodies may be chimeric antibodies, humanized antibodies, single chain antibodies, or fragments thereof. A further embodiment provides for an immortal cell line that produces a monoclonal antibody that is specific for PlyA or biologically active subunits or fragments thereof.

Diagnostic Uses

Accordingly another aspect of the invention provides for methods of diagnosing a pathogenic streptococcal infection. In a specific embodiment, a clinical sample suspected of harboring Group A streptococcus cells is pretreated with a PlyA polypeptide provided herein. Pretreatment of the clinical sample lyses Group A streptococcus cells, if present in the sample, rendering cell lysate components accessible to antibodies used in detection.

Diagnostic testing formats, including ELISA assays, lateral flow assays, or radioimmunoassays may be contemplated for use with the present invention. In these formats, one may utilize a PlyA protein directly or one may prepare antibodies to such protein as noted herein for use in kits to monitor the presence of pathogenic streptococci in a patient sample. The procedures for ELISA or radioimmunoassays are known to those skilled in the art.

In one embodiment, the binding domain of PlyA is labeled, e.g., with a fluorescent chemical or protein and the labeled PlyA is then incubated directly with a sample taken from a subject suspected of harboring a pathogenic streptococci. The observation of fluorescence (or other detection of substrate binding) in the sample is indicative of the presence of a pathogenic streptococcal infection. A yet further embodiment provides for the use of PlyA in a luciferin-luciferase assay to aid in diagnosing pathogenic streptococcal infections. In this assay format, a sample suspected of harboring a pathogenic streptococcus is incubated directly with the PlyA. If the sample contains a pathogenic streptococcus, PlyA will bind to the bacteria, resulting in lysis of the bacteria and subsequent release of ATP or other components normally present in the cytoplasm of the bacterial cell, such as enzymes. The lysate is then tested in a luciferin-luciferase assay. In another embodiment, the sample suspected of harboring a pathogenic streptococcus may be added directly to PlyA concurrently with luciferin-luciferase without the need to collect the cell lysate first before adding it to the luciferin-luciferase. If a pathogenic streptococcus is present in the sample, the release of ATP from the lysed bacteria will trigger a positive reaction in the luciferin-luciferase system, resulting in release of measurable light from the reaction mixture. In another embodiment, any other cytoplasmic markers, enzymes, proteins, cell wall fragments, or carbohydrates liberated by PlyA from streptococci could also be detected by any methodologies common to the diagnostic art.

Alternatively, one embodiment of the invention may use an antibody to a PlyA polypeptide or to subunits or fragments thereof, and the antibody may be labeled (eg. with fluorescein or other known fluorescent proteins or chemicals), coupled to the bacteriophage protein and used to monitor binding of the specific protein to the bacteria in a patient sample, thus aiding in detection of pathogenic streptococci. A polypeptide may be labeled directly and used to detect the presence of pathogenic streptococci in a patient sample.

Further diagnostic testing formats, including ELISA assays or radioimmunoassays may also be contemplated for use with the present invention. In these formats, one can utilize a Ply polypeptide directly or one may prepare antibodies to these proteins as noted herein for use in kits to monitor the presence of pathogenic streptococci in a patient sample. The procedures for ELISA or radioimmunoassays are known to those skilled in the art.

A further aspect of the invention provides for a method of diagnosing a pathogenic streptococcal infection, comprising: a) collecting a patient sample suspected of harboring a streptococcus; b) contacting the sample with a fluoresceinated PlyA; and c) measuring the amount of fluoresceinated polypeptide bound to the sample, wherein the detection of binding indicates the presence of streptococci in the sample.

A yet further aspect of the invention provides for a method for detecting the presence of streptococci in a sample, comprising: a) collecting a patient sample suspected of harboring a streptococcus; b) incubating the sample with the PlyA; c) collecting the cell lysate; d) incubating the cell lysate with luciferin-luciferase; and e) measuring the amount of light produced, wherein an increase in the amount of light produced is indicative of the presence of streptococci in the sample.

A yet further aspect of the invention provides for a method for detecting the presence of streptococci in a sample, comprising: a) collecting a patient sample suspected of harboring a streptococcus; b) incubating the sample in the presence of luciferin-luciferase along with the PlyA; and c) measuring the amount of light produced, wherein an increase in the amount of light produced is indicative of the presence of streptococci in the sample.

A yet further aspect of the invention provides for generation of antibodies to the PlyA or subunits or fragments thereof. The antibodies may be polyclonal, monoclonal, chimeric, humanized, or single chain antibodies. They may be prepared in animals such as mice, rats, guinea pigs, rabbits, goats, sheep, horses, and pigs. These antibodies may be used for identification and isolation of the components of the streptococcal cell wall to which the PlyA binds. An additional use of these antibodies may be for mobilizing the PlyA to a Biacore chip to perform studies on the affinity or kinetics of binding of the PlyA to its binding site on the streptococcal cell wall.

A yet further aspect of the invention would be to use the PlyA to lyse the streptococcus in the infection, which will release the DNA of the streptococcus. This released DNA can then be utilized for PCR analysis to identify the streptococcus. A more particular embodiment of the invention is a method for detection of pathogenic streptococci in a sample, comprising: a) collecting a sample from a patient suspected of having a streptococcal infection; b) adding the PlyA into the sample until lysis of bacteria is observed; c) isolating the DNA from the lysed bacteria; d) utilizing the isolated DNA for preparation of a probe which can be utilized for analysis and identification of the presence of streptococcus in a patient sample.

Therapeutic Uses

Another aspect of the invention provides for the use of the PlyA (lysin) polypeptide in treatment of bacterial infections or in prevention of bacterial cell growth in vitro and in vivo. One embodiment of the invention features use of the PlyA (lysin) polypeptide to treat infections caused by streptococci or to prevent growth of streptococci, in particular streptococci from group A. A further aspect of this invention provides for use of the PlyA lysin as a decontamination agent.

The invention provides for treatment or prevention of various diseases and disorders by administration of PlyA. The administration of PlyA would be by way of a pharmaceutically acceptable carrier. The administration of PlyA may be by way of the oral cavity or it may be delivered parenterally. The PlyA may be administered for use as an anti-infective and may be delivered topically, mucosally or sublingually. For systemic infections, it may be delivered intravenously, intramuscularly, or subcutaneously.

In a further embodiment, treatment of infections of the upper respiratory tract can be prophylactically or therapeutically treated with a composition comprising an effective amount of PlyA, and a carrier for delivering PlyA to a mouth, throat, or nasal passage. It is preferred that PlyA is in an environment having a pH that allows for activity of PlyA. If an individual has been exposed to someone with an upper respiratory disorder, PlyA will reside in the mucosal lining and prevent any colonization of the infecting bacteria.

Means of application include, but are not limited to direct, indirect, carrier and special means or any combination of means. Direct application of PlyA may be by nasal sprays, nasal drops, nasal ointments, nasal washes, nasal injections, nasal packings, bronchial sprays and inhalers, or indirectly through use of throat lozenges, or through use of mouthwashes or gargles, or through the use of ointments applied to the nasal nares, the bridge of the nose, or the face or any combination of these and similar methods of application. The forms in which PlyA may be administered include but are not limited to lozenges, troches, candies, injectants, chewing gums, tablets, powders, sprays, liquids, ointments, and aerosols.

The lozenge, tablet, or gum into which the PlyA is added may contain sugar, corn syrup, a variety of dyes, non-sugar sweeteners, flavorings, any binders, or combinations thereof. Similarly, any gum based products may contain acacia, carnauba wax, citric acid, corn starch, food colorings, flavorings, non-sugar sweeteners, gelatin, glucose, glycerin, gum base, shellac, sodium saccharin, sugar, water, white wax, cellulose, other binders, and combinations thereof.

Lozenges may further contain sucrose, corn starch, acacia, gum tragacanth, anethole, linseed, oleoresin, mineral oil, and cellulose, other binders, and combinations thereof. In another embodiment of the invention, sugar substitutes are used in place of dextrose, sucrose, or other sugars.

The PlyA may also be placed in a nasal spray, wherein the nasal spray is the carrier. The nasal spray can be a long acting or timed release spray, and can be manufactured by means well known in the art. An inhalant may also be used, so that the PlyA may reach further down into the bronchial tract, including into the lungs.

Another composition and use of the PlyA is for the therapeutic or prophylactic treatment of bacterial infections of burns and wounds of the skin. The composition comprises an effective amount of the PlyA and a carrier for delivering PlyA to the wounded skin. The mode of application for the PlyA includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes but is not limited to a smear, spray, a time-release patch, a liquid absorbed wipe, and combinations thereof. The PlyA may be applied to a bandage either directly or in one of the other carriers. The bandages may be sold damp or dry, wherein the PlyA is in a lyophilized form on the bandage. This method of application is most effective for the treatment of burns.

In a further embodiment wherein a bacteriocidal activity is desirable, PlyA is administered alone or in combination with one or more additional therapeutic compounds or treatments. In a preferred embodiment, PlyA can be administered to a human subject for therapy (e.g. to ameliorate symptoms or to retard onset or progression) of bacterial infections. One embodiment provides for treatment of streptococcal pharyngitis. A further embodiment provides for the PlyA lysin to be administered to non-human or human mammals. It is also envisioned that one embodiment may provide for treatment of mammals, including human subjects and non-human mammals, suffering from streptococcal infections and who are not responsive to more traditional modes of anti-microbial therapy. It is also envisioned that the PlyA may be used for decontamination purposes. It is also envisioned that the PlyA may be administered along with other lytic enzymes or with other antibiotics or anti-microbial forms of therapy.

The PlyA for use in therapy can be tested in suitable animal model systems prior to testing in humans, including but not limited to rats, mice, chicken, cows, horses, monkeys, rabbits, etc. For in vivo testing, prior to administration to humans, any animal model system known in the art may be used. In one embodiment, PlyA are tested in non-human animals (e.g., mice, rats, monkeys, rabbits, and guinea pigs), preferably non-human animal models for streptococcal infectious diseases. In accordance with this embodiment, PlyA is administered to the animals, and the effect of the PlyA on microbial levels is determined in the infected animal. Active PlyA can be identified by comparing the level of bacteria in a culture obtained from an animal or group of animals treated with PlyA with the level of the bacteria in a culture obtained from an animal or group of animals treated with a control nucleic acid or protein.

In yet another embodiment, test compounds that modulate the activity of PlyAs are identified in human subjects having an infection associated with streptococcal bacteria. In accordance with this embodiment, a test compound or a control compound is administered to the human subject in conjunction with the PlyA, and the effect of a test compound on either reduction in spread of the microbial infection, elimination of the bacterial infection or amelioration of symptoms.

Therapeutic and Prophylactic Compositions and Their Use

The invention provides methods of treatment comprising administering to a subject an effective amount of PlyA. In a preferred aspect, the PlyA is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject.

Various delivery systems are known and can be used to administer the PlyA, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutancous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment, such as topical use on the skin; any suitable method known to the art may be used.

Another aspect of the invention provides for pharmaceutical compositions comprising the PlyA for therapeutic use in treatment of bacterial infections. Moreover, a further embodiment may include a pharmaceutical composition designed for use in topical treatment of bacterial infections. Another embodiment may include a pharmaceutical composition designed for use in treatment of systemic infections, or infections that are non-responsive to other antibiotic modalities.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid of A25 bacteriophage or PlyA, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the PlyA which will be effective in the treatment of infectious diseases, can be determined by standard clinical techniques based on the present description. In addition, its vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In another embodiment, the PlyA can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.)

In yet another embodiment, the PlyA can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

EXAMPLES

Example 1

Expression and Purification of rA25 Lysin Protein in *E. coli*

To facilitate expression/purification of the S, pyogenes phage A25 lysin in a heterologous *E. coli* host, the lysin gene was genetically engineered for insertion into the expression vector pET25a such that a C-terminal His-tagged fusion protein would be encoded. As a result, the A25 termination codon was deleted. The fusion protein was designed to allow initiation at the presumed authentic A25 lysin initiation codon for the amino acid residue methionine The His-tag would permit purification with Ni-NTA chromatography resin (Qiagen). The engineered fragment was first propagated in a non-expressing vector and the DNA sequence was confirmed before transferring the fragment to the pET25a vector.

For expression, Terrific Broth with 50 µg/mL Ampicillin was inoculated with *E. coli* Origami (Novagen) containing pET 21a LysNX and incubated at 37° C. overnight to stationary phase while shaking at 250 RPM. The following day, a subculture was prepared in Terrific Broth with 50 µg/mL Ampicillin at $OD_{550\ nm}$ of ~0.15. The culture was incubated at 37° C. while shaking at 250 RPM until $OD_{50\ nm}$ reached 0.6, and then rA25 Lysin expression was induced by adding IPTG to 1 mM. Incubation continued for 3 hours at 30° C. while shaking at 250 RPM. Cells were harvested by centrifugation at 7700×g for 15 minutes at 2 to 8° C. Supernatant was discarded and the pellet was washed with Extraction Buffer (0.3M NaCl, 50 mM $NaPO_4$, and 10 mM Imidazole, pH 8.0), then centrifuged at 6000×g for 10 minutes at 2 to 8° C. The supernatant was discarded and washed as above 2 more times. After the $3^{rd}$ wash, the supernatant was discarded and the pellet was stored at −20° C.

For sonication, the frozen pellet was resuspended in chilled Extraction Buffer containing 1 mM PMSF at a volume $\frac{1}{40}$th that of the original batch culture. The cell suspension was sonicated on ice with a Branson Sonifier 450 for a total of 7 cycles (one cycle was 4 minutes with pulsing, Duty cycle ~30% and Output on setting 3). Following complete sonication, the suspension was centrifuged at 10,000×g for 25 minutes at 2 to 8° C. Sonic supernatant was decanted and mixed with Ni-NTA Superflow resin (Qiagen) for bulk purification, according to manufacturer's instructions. The mixture was gently rocked at 4° C. for 2 hours. A clean column was first washed with Extraction Buffer. The mixture was added to the column, washed with Wash Buffer (0.3 M NaCl, 50 mM $NaPO_4$, and 20 mM Imidazole, pH 8.0), and rA25 was eluted with Elution Buffer (0.3 M NaCl, 50 mM $NaPO_4$, and 250 mM Imidazole, pH 8.0). The eluate was dialyzed against KEB Buffer (0.1M $KPO_4$, 5 mM EDTA, and 3 mM β-ME, pH 6.7). Following dialysis, the eluate was removed from tubing and clarified, then concentrated to approximately 10 mg/mL. Purity was evaluated by SDS-PAGE.

Example 2 rPlyA Treament of Group A Streptococci Releases Intact Group A Antigen Enabling Detection in a Lateral Flow Assay Specific for Group A Antigen After the indicated treatments, Group A Streptococci were applied to a lateral flow device enabling detection of the Group A antigen. 715:78

Figure 6:
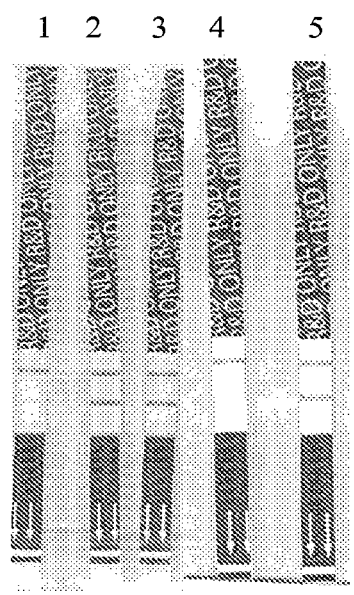
FIG. 6 shows a later flow device showing that rPlyA treament of Group A Streptococci releases intact Group A antigen enabling detection in a lateral flow assay specific for Group A antigen.

The results are shown in FIG. 6 as follows:
Lane 1: no addition
Lane 2: 5 µg rPlyA prep 08.08
Lane 3: 15 µg rPlyA prep D
Lane 4: 5 µg rPlyA prep 08.08 without Group A Streptococcus
Lane 5: replicate of lane 2

This experiment demonstrates that rPlyA enables Group A Streptococcus detection in this assay format. No previous publications had demonstrated the suitability of a lysin from a Group A-specific phage for this purpose. Availability of the recombinant rPlyA facilitates these kinds of experiments; use of the native lysin would have required considerably more complex protein purification and it would not be suitable as a manufacturing process.

Example 3

The Lysin Gene is Contained within Bacteriophage A25

The lysin gene is contained within bacteriophage A25, whose DNA sequence had not been previously disclosed. Experiments were performed to identify and isolate the lysin gene within this genome using standard recombinant DNA procedures and also PCR and comparative genomics. The complete DNA sequence of the 1446 bp gene was determined. The encoded lysin was then expressed as a recombinant protein in *E. coli* and the recombinant lysin was then purified to homogeneity. The purified lysin was evaluated biochemically, and its ability to rapidly lyse live Group A Streptococcus bacteria was determinined. Its performance was then evaluated in an in vitro immunodiagnostic test designed to detect Group A Streptococcus bacteria.

Example 4

Experimental

Isolate phage DNA (618:61)
Qiagen QIAmp mini kit.
DNA was isolated from clarified, purified A25 bacteriophage suspensions with the Qiagen QIAamp mini kit. The suspension was treated with DNaseI (20 µg/ml) for 15 minutes and then centrifuged five minutes at 18,000×g. The suspension was adjusted to 20 mM EDTA and then treated with 50 µg/ml proteinase K in an equal volume of Qiagen solution AL for 10 minutes at 56° C. DNA was then purified according the manufacturer's instructions.
HindIII digestion (618:62)
Purified A25 phage DNA was treated with HindIII restriction endonuclease and the digested DNA was analyzed by agarose gel electrophoresis. Fragments of about 4, 10, and 17 Kb were detectable, a similar pattern to those previously reported (Pomrenke and Ferretti).
Molecular cloning of HindIII fragments; partial DNA sequencing
HindIII fragments derived from A25 were propagated in E. coli as recombinant DNA molecules in the vector pUC19. DNA sequences at fragment termini were determined with flanking-sequence primers complementary to pUC19.

Example 5

In vitro bacteriocidal activity of A25 lysin

Lysin activity was determined by a modification of a described turbidity reduction assay (Fischetti V A, et al J Exp Med. 1971 May 1; 133(5):1105-17). Stationary or log phase cultures of Group A streptococcus strain 12204 grown in Todd-Hewitt broth was centrifuged and washed once with 0.05M phosphate buffer, pH 6.7, containing 0.005M EDTA. The washed cells were resuspended in the same buffer to an OD of about 0.3 at 600 nm in a (spectrophotometer). Lysin assays were performed at room temperature in covered microtiter plates.

Chloroform-killed Group A streptococcus strain 12204 was also a suitable substrate for the phage lysin. Cell walls were prepared by a modification of published procedures (Hill J E and L W Wannamaker 1981 J. Bact. 145: 696). L3 broth cultures were adjusted to 5% (vol/vol) chloroform and incubated with shaking at 37° C. for 3 hours. Cell suspensions were decanted away from the chloroform and then the cells were sedimented and suspended in 0.1M phosphate buffer (pH 6.7) containing 0.005M EDTA and 3 mM 2-mercaptoethanol. Killed-cell suspensions were adjusted to a turbidity of ~0.2 in the spectrophotometer used for the lysin assays. Killed-cell lysin assays were performed at 37° C. in microtiter plates.

The susceptibility of other bacterial species to lysis by the A25 lysin was also monitored by a reduction in turbidity assay as described above. There was no detectable lytic activity on the following bacteria: *Staphylococcus aureus, Staphylococcus epidermis, Neisseria.* rA25 lysin activity was also measured in Group A Streptococcus ICT devices which depended on the lysin's ability to rapidly lyse Group A Streptococcus and extract a sufficient level of antigen for detectability by ICT.

Example 6

Experimental

The sequences of lysin genes from various bacteriophages have been determined (with varying extents of similarity among them). We decided to find a gene in the A25 genome whose DNA would encode a protein whose sequence was sufficiently similar to one of those sequenced lysin genes to allow identification. Many of these sequences are available in public Internet databases.

The main obstacle was that the DNA sequence of the phage genome had not been previously reported. The strategy that was selected to overcome that obstacle was to isolate (by molecular cloning) any fragment of the phage genome and determine its DNA sequence. Then the Internet database would be searched to identify a related sequence in another bacteriophage. It would then be hypothesized that the order of genes in phage A25 would be the same as in that phage. Then standard approaches (e.g. restriction endonuclease mapping) could be used to identify fragments likely to contain the lysin gene.

In Pomrenke M E and Ferretti J J. Physical maps of the streptococcal bacteriophage A25 and C1 genomes. J. Basic Microbiol. 29 (1989) 6, 395-398, phage A25 DNA had reportedly been isolated and the locations of sites susceptible to digestion with several restriction endonucleases (EcoRI, AvaI, HindIII) had been determined. Based on that analysis, the size of the phage genome was listed as 34,600 nucleotide pairs. When we digested purified A25 phage DNA with these enzymes, only the pattern with HindIII was similar to the ones reported. We proceeded to isolate these DNA fragments by molecular cloning, i.e., recombinant DNA (rDNA) methodology. We then used a partial DNA sequence of one of these fragments to identify a related bacteriophage in the Internet database as outlined above.

Plasmid pA25H4 contained a 4 kB HindIII fragment in the pUC19 vector. DNA sequencing of the termini of the 4 kB fragment, and subsequent BLAST analysis, revealed the "best" match (~70%) on both ends was to Streptococcus pneumoniae bacteriophage MM1 1998 (Accession # DQ113772), whose complete genome sequence had been determined. On one end, the match was to a "minor capsid" protein at MM1 1998 coordinate 20959. At the other end, the match was within the MM1 1998 "tape measure" protein gene, at coordinate 25205. Thus the match on both ends was to loci also separated by 4 kB in MM1 1998. Based on this pattern of consistent similarity over 4kB it was hypothesized that phage A25 was similar to MM1 1998 throughout its genome. In phage MM1 1998, the lysin gene is located very near the "right" terminus, so efforts were directed at obtaining the corresponding rDNA.

It was presumed (based on Pomrenke and Ferretti) that the right terminus of phage A25 was also the terminus of the 10 kB "HindIII" fragment. After propagation of this fragment in E. coli vector pUC19, as plasmid pA25H10, the DNA sequence at the termini of this fragment was determined as described above. The DNA sequence at one end confirmed that the HindIII site at this end was the same one within the "tape measure" gene homologue at the end of the insert in pA25H4. Thus, in the phage A25 genome, the 10 kB HindIII fragment was adjacent to the 4 kB fragment in pA25H4. However, the DNA sequence at the other end was not the lysin gene-containing phage terminus, but rather another HindIII site. BLAST analysis with this DNA sequence did not produce any homology with MM1 1998. However, the best homologies, although weak, were to various GAS prophages in the region just before their holin genes. Since in most bacteriophage genomes the holin gene is adjacent to the lysin gene, strategies were pursued enabling isolation of the adjacent, presumably small, presumably terminal DNA region.

Since there was an unexpected HindIII site (not predicted by Pomrcnkc and Ferretti) near the presumptive end of phage A25, the 10 kB fragment in pA25H10 was subjected to restriction analysis to locate another candidate enzyme to facilitate molecular cloning of the phage terminus. Restriction endonuclease NheI was selected, and was predicted to produce a conveniently sized terminal fragment of about 2 kB. When phage A25 NheI fragments of about that size were molecularly cloned, plasmid pNhe7 was identified. DNA sequencing of pNhe7 did reveal that one end of this fragment was the expected one also found in pA25H10. Unfortunately, however, the other end of this fragment was another NheI site, rather than the phage terminus. But this end did contain a portion of the probable lysin gene (based on BLAST analysis), encoding the N-terminal 130 amino acid residues.

In order to isolate DNA containing the remainder of the A25 lysin gene, "PCR-walking" was used. In this method it is assumed that the DNA adjacent to the isolated segment continues to be related to the homologue. One PCR primer is then chosen from regions within the homologue which arc the most conserved (by BLAST analysis) and which would contain as much adjacent DNA as is thought to be needed. The other PCR primer is derived from the already isolated segment. The BLAST analysis of N-terminal A25 lysin identified the best homologue as locus SpyM3_1096, a putative lysin encoded in the genome of *Streptococcus pyogenes* MGAS315 (complement 1139031 . . . 1140245 of accession # AE014074.1). BLAST analysis with the C-terminal region of SpyM3_1096 revealed a region just "downstream" of this lysin gene which was conserved in several other GAS prophages at the same position relative to their lysin genes. Thus a PCR primer was prepared from this conserved region, in the event that this region was also conserved in the lytic phage A25. PCR (at reduced temperature) was performed on phage A25 with this primer and an authentic A25 lysin primer (derived from the sequence in pNhe7). Propagation of the resulting PCR product produced plasmid pE1. DNA sequencing of plasmid pE1 revealed that it did contain adjacent A25 lysin sequences, but it did not extend to the lysin terminus. Thus the PCR-walking approach was repeated after a BLAST analysis with the segment of the A25 lysin gene found in plasmid pE1. The best homologue to this large fragment of the lysin gene was with the lysin gene contained within Streptococcus suis phage SMP (accession # ABK91888.1). Although BLAST analysis with the SMP lysin C-terminal sequence and flanking regions identified some conserved regions, a PCR primer prepared directly from the sequence flanking the SMP lysin gene proved most useful in amplifying the remainder of the A25 lysin gene. Propagation of the resulting PCR product produced plasmid pC, which contained the complete A25 lysin gene. Subsequently the entire lysin gene was also isolated by molecular cloning of a restriction fragment derived directly from the phage genome. The reported lysin gene sequence was confirmed within this molecular clone.

We claim:

1. A method of detecting a Group A streptococcal analyte in a pathogenic streptococcal infection, comprising: a) providing a patient sample suspected of harboring Group A streptococci; b) contacting the sample with a PlyA polypeptide comprising an amino acid sequence with at least 85% sequence identity to SEQ ID NO: 2 and a purification tag, in an amount effective to lyse Group A streptococci if present in the sample; and c) detecting the presence or absence of a Group A streptococcal analyte present in the sample, wherein the presence of the Group A streptococcal analyte in the sample indicates the presence of a streptococcal infection in the subject.

2. The method of claim 1 wherein the PlyA polypeptide comprises SEQ ID NO: 2 and a purification tag.

3. A method of detecting a bound PlyA polypeptide in a pathogenic streptococcal infection, comprising: a) providing a patient sample suspected of harboring Group A streptococci; b) contacting the sample with a PlyA polypeptide comprising an amino acid sequence with at least 85% sequence identity to SEQ ID NO: 2 and a purification tag; and c) detecting the presence or absence of the PlyA polypeptide bound to a PlyA substrate if present in the sample, wherein the detection of binding indicates the presence of Group A streptococci in the sample.

4. The method of claim 3 wherein the PlyA polypeptide comprises SEQ ID NO: 2 and a purification tag.

5. The method of claim 1, wherein the PlyA polypeptide comprises an amino acid sequence with at least 90% sequence identity to SEQ ID NO:2.

6. The method of claim 1, wherein the PlyA polypeptide comprises an amino acid sequence with at least 95% sequence identity to SEQ ID NO:2.

7. The method of claim 1, wherein the PlyA polypeptide comprises an amino acid sequence with at least 99% sequence identity to SEQ ID NO:2.

8. The method of claim 3, wherein the PlyA polypeptide comprises an amino acid sequence with at least 90% sequence identity to SEQ ID NO:2.

9. The method of claim 3, wherein the PlyA polypeptide comprises an amino acid sequence with at least 95% sequence identity to SEQ ID NO:2.

10. The method of claim 3, wherein the PlyA polypeptide comprises an amino acid sequence with at least 99% sequence identity to SEQ ID NO:2.

* * * * *

SEQUENCE LISTING

```
<160> NUMBER OF SEQ ID NOS: 2

<210> SEQ ID NO 1
<211> LENGTH: 1446
<212> TYPE: DNA
<213> ORGANISM: Bacteriophage A25

<400> SEQUENCE: 1
atggcaatag agactgaaaa agccatttct tggatggtag ctagacaagg ggctgtttct      60
tattccatgg attaccgaaa tggtccaagc tcctatgact gctcaagtgc tatttattat     120
gctttgatgt cagcaggtgc tatctctgct ggctgggctg taaatacaga atatatgcat     180
gattggctta tcaaaaatgg atatgtattg attgcagaaa atcaagattg gaatagccaa     240
aggggtgatg ttgttatttg ggggctacgt ggtcagtctg ctggagctgg tggtcatgtc     300
gtaatgtttg tagattcaga caacatcatt cactgtaatt atgccaataa tggcattacc     360
atcaataact acaatcagac cgctgctagc gctggctgga tgtattctta tgtttaccgt     420
ttagccaccc cagcaacaac ttcaacggct gggaaaagtc tcgatacctt agttaaggaa     480
accttggctg gtaactacgg taacgagaa atgcgtaagg cagcccttgg taatcaatat     540
gatgctgtca tggtagtcat caatggcaaa tctacgacag ctcaaaagtc agttgaccaa     600
ctggcgcagg aagtgattgc tggtaagcac ggtaacggtg aaggccgtaa aaaggcactt     660
gggagccagt atgacgctgt tcaaaagaga gtaaccgaaa tgctaaaaac tagtacatca     720
ggaaacacct ctaaaacacc atcagagcca tctaatagcg tggtgtaaa ttcatccacc     780 gaacccaaga cagaggaaac tggggcaact ggtaaagcga cagataccaa aatcactaaa     840
```

```
gaagatggtg acttgtcctt taacggtgca atcctgaaaa aatctgtcct tgatgttatc    900
cttgctaagt gtaaggaaca caatatccta cctagctacg ctattaccgt tctacacttt    960
gagggctttt ggggtaccct cagccgtaggt aaggcagata caactgggg aggcatgaca   1020 tggactggta aggagagcg tccaagtggt gtgactgtca cccaaggaac agcaagacca   1080
gctaatgagg gtggacatta tatgcactat gcctctgtag atgactttct tacagattgg   1140
```



```
gaagatggtg acttgtcctt taacggtgca atcctgaaaa aatctgtcct tgatgttatc    900
cttgctaagt gtaaggaaca caatatccta cctagctacg ctattaccgt tctacacttt    960
gagggctttt ggggtaccct cagccgtaggt aaggcagata caactgggg aggcatgaca   1020 tggactggta aggagagcg tccaagtggt gtgactgtca cccaaggaac agcaagacca   1080
gctaatgagg gtggacatta tatgcactat gcctctgtag atgactttct tacagattgg   1140
ttctacctgc tacgttcagg aggtagctac aaggtttcag gagccaaaac ctttagcgat   1200
gctgtcaaag gcatgtttaa agtcggtggg tctgtctatg attatgctgc tagcggcttt   1260
gatagctaca tcgttggagc ttccagccgt ctcaaggcta ttgagcagga aacggttct   1320 ttggacaagt ttgataaagc taccgacatt ggtgtcggta gcaaagacca gattgacatt   1380
accattgcag gtattgaagt taccatcaat ggtatcactt atgaactgac taaaaagcca   1440
gtttga                                                              1446
```

<210> SEQ ID NO 2
<211> LENGTH: 482
<212> TYPE: PRT
<213> ORGANISM: Bacteriophage A25

<400> SEQUENCE: 2

```
Met Ala Ile Glu Thr Glu Lys Ala Ile Ser Trp Met Val Ala Arg Gln
1               5                   10                  15

Gly Ala Val Ser Tyr Ser Met Asp Tyr Arg Asn Gly Pro Ser Ser Tyr
            20                  25                  30

Asp Cys Ser Ser Ala Ile Tyr Tyr Ala Leu Met Ser Ala Gly Ala Ile
        35                  40                  45

Ser Ala Gly Trp Ala Val Asn Thr Glu Tyr Met His Asp Trp Leu Ile
    50                  55                  60

Lys Asn Gly Tyr Val Leu Ile Ala Glu Asn Gln Asp Trp Asn Ser Gln
65                  70                  75                  80

Arg Gly Asp Val Val Ile Trp Gly Leu Arg Gly Gln Ser Ala Gly Ala
                85                  90                  95

Gly Gly His Val Val Met Phe Val Asp Ser Asp Asn Ile Ile His Cys
            100                 105                 110

Asn Tyr Ala Asn Asn Gly Ile Thr Ile Asn Asn Tyr Asn Gln Thr Ala
        115                 120                 125

Ala Ser Ala Gly Trp Met Tyr Ser Tyr Val Tyr Arg Leu Ala Thr Pro
    130                 135                 140

Ala Thr Thr Ser Thr Ala Gly Lys Ser Leu Asp Thr Leu Val Lys Glu
145                 150                 155                 160

Thr Leu Ala Gly Asn Tyr Gly Asn Gly Glu Met Arg Lys Ala Ala Leu
                165                 170                 175

Gly Asn Gln Tyr Asp Ala Val Met Val Ile Asn Gly Lys Ser Thr
            180                 185                 190

Thr Ala Gln Lys Ser Val Asp Gln Leu Ala Gln Glu Val Ile Ala Gly
        195                 200                 205

Lys His Gly Asn Gly Glu Gly Arg Lys Lys Ala Leu Gly Ser Gln Tyr
    210                 215                 220

Asp Ala Val Gln Lys Arg Val Thr Glu Met Leu Lys Thr Ser Thr Ser
225                 230                 235                 240

Gly Asn Thr Ser Lys Thr Pro Ser Glu Pro Ser Asn Ser Val Val Val
                245                 250                 255

Asn Ser Ser Thr Glu Pro Lys Thr Glu Glu Thr Gly Ala Thr Gly Lys
```

-continued

```
                260                 265                 270
Ala Thr Asp Thr Lys Ile Thr Lys Glu Asp Gly Asp Leu Ser Phe Asn
            275                 280                 285

Gly Ala Ile Leu Lys Lys Ser Val Leu Asp Val Ile Leu Ala Lys Cys
            290                 295                 300

Lys Glu His Asn Ile Leu Pro Ser Tyr Ala Ile Thr Val Leu His Phe
305                 310                 315                 320

Glu Gly Leu Trp Gly Thr Ser Ala Val Gly Lys Ala Asp Asn Asn Trp
                325                 330                 335

Gly Gly Met Thr Trp Thr Gly Lys Gly Glu Arg Pro Ser Gly Val Thr
            340                 345                 350

Val Thr Gln Gly Thr Ala Arg Pro Ala Asn Glu Gly Gly His Tyr Met
            355                 360                 365

His Tyr Ala Ser Val Asp Asp Phe Leu Thr Asp Trp Phe Tyr Leu Leu
        370                 375                 380

Arg Ser Gly Gly Ser Tyr Lys Val Ser Gly Ala Lys Thr Phe Ser Asp
385                 390                 395                 400

Ala Val Lys Gly Met Phe Lys Val Gly Gly Ser Val Tyr Asp Tyr Ala
                405                 410                 415

Ala Ser Gly Phe Asp Ser Tyr Ile Val Gly Ala Ser Ser Arg Leu Lys
            420                 425                 430

Ala Ile Glu Gln Glu Asn Gly Ser Leu Asp Lys Phe Asp Lys Ala Thr
            435                 440                 445

Asp Ile Gly Val Gly Ser Lys Asp Gln Ile Asp Ile Thr Ile Ala Gly
        450                 455                 460

Ile Glu Val Thr Ile Asn Gly Ile Thr Tyr Glu Leu Thr Lys Lys Pro
465                 470                 475                 480

Val Leu
```